United States Patent
Ouwerkerk et al.

Patent Number: 5,652,433
Date of Patent: Jul. 29, 1997

[54] BISTABLE SWITCHING DEVICE CONTAINING GADOLINIUM HYDRIDE

[75] Inventors: Martin Ouwerkerk; Paul Van Der Sluis, both of Eindhoven, Netherlands

[73] Assignee: U.S. Philips Corporation, New York, N.Y.

[21] Appl. No.: 653,960

[22] Filed: May 28, 1996

[30] Foreign Application Priority Data

May 30, 1995 [EP] European Pat. Off. ............ 95201408
Dec. 22, 1995 [EP] European Pat. Off. ............ 95203611

[51] Int. Cl.⁶ .......................... H01L 47/00; G02F 1/15
[52] U.S. Cl. ......................... 257/1; 257/2; 250/331; 359/265; 359/273
[58] Field of Search ............... 257/1, 2; 250/331.1; 359/265, 273

[56] References Cited

U.S. PATENT DOCUMENTS

| | | | |
|---|---|---|---|
| 4,818,080 | 4/1989 | Glasheen | 350/355 |
| 4,999,321 | 3/1991 | Kohli | 501/42 |
| 5,069,535 | 12/1991 | Baucke et al. | 359/273 |
| 5,202,786 | 4/1993 | Boyle et al. | 359/243 |

*Primary Examiner*—Michael J. Tokar
*Assistant Examiner*—Andrew W. Seacord, II
*Attorney, Agent, or Firm*—John C. Fox

[57] ABSTRACT

A description is given of a switching device 1 comprising a transparent substrate 3, a switching film 5 of gadolinium having a thickness of 200 nm and a palladium layer (7) having a thickness of 10 nm. Under the influence of hydrogen gas, a transparent semiconductive layer (5) of $GdH_x$ ($x>2$) is formed which can be converted into a non-transparent layer of $GdH_x$ ($x<2$) by means of evacuation. The conversion between both compositions is reversible, and this phenomenon can for example be used in an optical switching element, a hydrogen sensor and thin displays.

7 Claims, 1 Drawing Sheet

BISTABLE SWITCHING DEVICE CONTAINING GADOLINIUM HYDRIDE

BACKGROUND OF THE INVENTION

The invention relates to a switching device comprising a substrate and a thin switching film containing a metal compound. The invention also relates to applications of such a switching device.

In the relevant switching devices, the electrical and/or optical properties are governed by external influences, such as mechanical stress or electric voltage, gas pressure, relative humidity, concentration etc.

For example, electrochromic devices are well-known, in which a layer of an electrochromic material, such as $MoO_3$, is sandwiched between two transparent electroconductive electrode layers, for example, of indium-tin oxide. A layer of an $H^+$- or $Li^+$-ion-conducting material is present between an electrode and the electrochromic material. The device often also comprises a counter electrode for storing ions. The application of the electric potential of several volts across the electrodes causes the transmission of the layer packet to change. Said transmission change is reversal. Electrochromic materials are used, for example, in variable-transmission windows for buildings and anti-dazzle mirrors in cars.

A drawback of oxidic electrochromic devices is that an extensive layer stack is required for their operation. A further important disadvantage is that such materials enable only a small transmission change, and hence a small contrast, to be attained.

OBJECTS AND SUMMARY OF THE INVENTION

It is an object of the invention to provide, inter alia, a switching device in which the switching film can be reversibly converted from the non-transparent to the transparent state. Both states must be stable. In addition, it must be possible to perform said conversion relatively rapidly at common temperatures and a common pressure. Besides, the switching device should have a simple layer structure.

In accordance with the invention, this object is achieved by a switching device as described in the opening paragraph, which is characterized in accordance with the invention in that the metal compound a contains gadolinium hydride phase which can be reversibly switched from a low hydrogen content metallic composition to a supersaturated hydrogen-rich semiconductive composition by an exchange of hydrogen.

It has been found that gadolinium in a thin film can form hydrides with hydrogen, which hydrides can be in the metallic state and in the semiconductive state, dependent upon the hydrogen content. In the metallic state, the thin film, i.e. the switching film, is non-transparent and reflective, whereas in the semiconductive state the switching film is transparent.

If a thin gadolinium switching film is exposed at room temperature to atomic hydrogen, the hydride phase $GdH_x$ is formed. At low hydrogen content (x<2), the film has a metallic character, and is electroconductive and non-transparent. At sufficiently high hydrogen pressures (>1 mbar), the supersaturated hydrogen-rich composition (x>2) is formed within 0.1 s. Said hydrogen-rich film (x>2) formed is transparent and of a yellow color in transmission.

The transition from the metallic composition to the semiconductive composition cannot only be demonstrated optically but also by means of a Hall-effect measurement and an electric resistance measurement.

Both gadolinium compositions are stable at room temperature. In the following part of this document, the designations metallic and semiconductive compositions will be used for x<2 and x>2, respectively.

If molecular hydrogen is supplied to the switching film, said hydrogen must be dissociated to atomic H. The rate of dissociation can be increased by providing the surface of the switching film with a thin layer of palladium having a thickness, for example, of 5 nm. At said thickness, the palladium layer is discontinuous. The layer thickness is not critical and is chosen to be in the range between 2 and 25 nm. Thin layers of 2 to 10 nm are preferred, however, because the thickness of the palladium layer determines the maximum transmission of the switching device. At a layer thickness of 10 nm, the maximum transmission is 15 to 20%. In addition, the palladium layer protects the underlying switching layer against oxidation.

It has been found that the transmission of the switching device is governed by the hydrogen pressure: the transmission increases as the hydrogen pressure increases.

A discontinuous palladium layer, or another discontinuous catalytically active layer, is preferred, in particular, if the switching device is used as an electrical switching element as a result of a change in the electric resistance of the switching film as a function of the hydrogen pressure. In this case, the electric resistance of the switching device is governed predominantly by that of the switching layer.

Apart from palladium, other catalytically active metals which promote hydrogen dissociation, such as platinum and nickel, can be provided on the switching film.

The molecular hydrogen can be passed from a gas cylinder filled with $H_2$ to the switching film at room temperature in a simple manner. Within 50 ms, the non-transparent, metallic Gd film changes into a semiconductive transparent $GdH_x$ film (x>2). The bandgap of said composition is about 2.5 eV. After evacuation of hydrogen, the transparent film is not converted to metallic Gd but to a metallic $GdH_x$ film (x<2) which is not transparent. The latter conversion takes place within 1 s. Said conversions do not disturb or degrade the switching layer.

The conversion of the metallic to the semiconductive composition is reversible: by supplying hydrogen, the non-transparent $GdH_x$ film (x<2) is converted to a transparent $GdH_x$ film (x>2) which is converted to a non-transparent $GdH_x$ film (x<2) by heating and/or evacuation of hydrogen. Said conversions can take place at room temperature.

Atomic hydrogen can also be obtained in other ways, such as by electrolytic reduction of water at the switching layer in accordance with the following reaction:

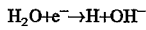

$$H_2O + e^- \rightarrow H + OH^-$$

Atomic hydrogen can also be generated from a hydrogen plasma. In this case, a catalytically active layer, for example, of palladium is not necessary. Atomic hydrogen can also originate from another metal hydride, such as metal alloys for hydrogen storage, which are known per se.

Alternatively, isotopes of hydrogen such as deuterium, as well as compounds with catalytically eliminable H-atoms such as methane, can be used instead of hydrogen.

The switching film in accordance with the invention is thin, i.e. its film thickness is less than 2 μm. The film thickness of the switching film preferably ranges between 100 and 1,000 nm. As hydrogen must diffuse in the switching film, the film thickness determines the rate of full conversion from the metallic to the semiconductive composition, and conversely. In the case of a film thickness of the switching film of 200 nm in combination with a 10 nm thick palladium layer, the conversion of, for example, $GdH_x$ ($x<2$) to $GdH_x$ ($x>2$) takes approximately 50 ms, whereas the backwards conversion takes place within 1 s. In particular the conversion of $GdH_x$ ($x<2$) to $GdH_x$ ($x>3$), in which an opaque film becomes transparent, is perceived as taking place instantaneously. A thinner or thicker film will lead, respectively, to a shorter or longer conversion time.

The switching film may optionally be composed of an alloy of gadolinium and another metal, for example copper. By means of these measures, the color, stability, velocity and electrical conductivity of the switching layer can be influenced.

Substrates to which the switching film can be adhered can be used as the substrate for the switching film. The substrates used in an optical switching element are transparent substrates, such as glass, quartz, diamond or aluminium oxide. The substrate may be even or curved.

The switching film is applied as a thin film to the substrate by means of conventional methods such as vacuum evaporation, sputtering, laser ablation, chemical vapour deposition or electroplating. In this respect, it is important that during and after application of the switching film, the metal of the switching film is not subject to oxidation. In a vacuum-evaporation process, this is achieved by maintaining the pressure, in particular, of the residual gases water and oxygen, at a low level below $10^{-6}$ to $10^{-7}$ mbar.

The catalytically active layer, for example, of Pd can alternatively be applied by means of one of the above-mentioned methods.

Apart from the above-mentioned (optical) change of the transmission, a change of the electric resistance of the switching film can be observed: the metallic composition has a much lower specific resistance than the semiconductive composition.

By virtue of the switch from a metallic, non-transparent state to a transparent, semiconductive state, and conversely, the switching device in accordance with the invention can be used in many applications.

By virtue of the optical effect, the switching device can be used as an optical switching element, for example as a variable beam splitter, and for controlling the illuminance or the shape of light beams in luminaires. Dependent upon the film thickness of the switching film, this film can exhibit almost zero transmission in the metallic state. This enables a switching device having a great contrast to be manufactured. The switching device can be used in applications in which electrochromic layers are presently being used, such as architectural glass, sun roofs and rear-view mirrors.

The switching device in accordance with the invention can also be used as a variable transmission filter for a display screen to improve the contrast.

By making a pattern on the gadolinium film in combination with a transparent counter electrode and an electrolyte, a thin display can be manufactured. The construction of such a display is much simpler than that of an LCD (liquid crystal display) due to the absence of an LC layer, orientation layer, retardation layer and polarization filter.

The switching film in accordance with the invention can also be used as a recording layer of an optical recording medium. A transparent semiconductive film can be locally converted to a non-transparent metallic film by means of thermal energy from a laser-light beam of sufficient power. If desired, the recorded information can be erased by supplying hydrogen.

As explained hereinabove, both the transmission and the electric resistance of the switching film are governed by the quantity of H in the switching film. By virtue thereof, the switching device in accordance with the invention can be used as an electrical switching element and as a sensor, indicator or actuator. In a rechargeable nickel-metal-hydride battery, the switching device can for example be used to indicate the cell voltage or cell pressure.

Some organic compounds, such as methane, eliminate H-atoms when they are in contact with a catalytically active metal such as palladium. The switching device in accordance with the invention then serves as a sensor for these organic compounds.

During the absorption of hydrogen in the switching film, an increase in thickness of approximately 11% takes place. The hydrogen absorption can be controlled electrically by means of an electrochemical cell. Thus, the switching device can be used as an actuator.

These and other aspects of the invention will be apparent from and elucidated with reference to the embodiments described hereinafter.

DESCRIPTION OF THE PREFERRED EMBODIMENTS

Exemplary Embodiment 1

Figure 1:
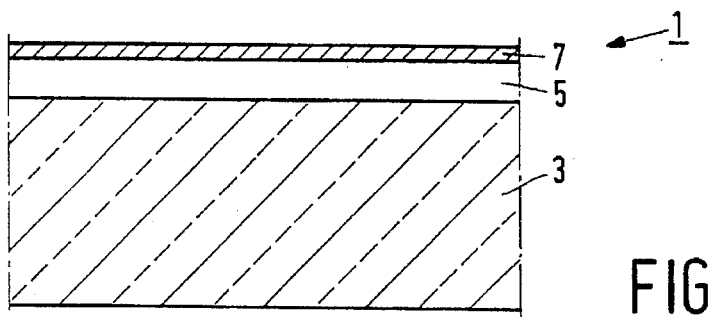
FIG. 1 is a schematic cross-sectional view of a switching device in accordance with the invention.

FIG. 1 is a schematic, cross-sectional view of a switching device 1 in accordance with the invention. A polished, quartz substrate 3 is provided with a 200 nm thick gadolinium layer as a switching film 5 by means of electron-beam evaporation. The residual pressure in the evaporation apparatus is less than $10^{-7}$ mbar. The deposition rate is 1.0 nm/s. In the same apparatus, a 10 nm thick palladium layer 7 is evaporated onto the switching film 5 by means of resistance heating at a deposition rate of 0.2 nm/s. Said switching film 5 has a metallic appearance and is non-transparent.

The sample comprised of the substrate 3, the switching layer 5 and the palladium layer 7 is arranged in a pressure cell provided with two windows of quartz glass. Said pressure cell also comprises connections for the supply of oxygen and for connecting it to a vacuum pump, respectively. The pressure cell is arranged in the sample room of a spectrophotometer. At wavelengths between 500 and 800 nm, the transmission T of the sample is 0.0%. After evacuation, the pressure cell is filled at room temperature with molecular hydrogen up to a pressure of 5 bar ($5.10^5$ Pa). The palladium layer 7 forms atomic H which is subsequently absorbed in the switching film 5. Within 50 ms, the transmission of the sample increases substantially to a value of approximately 13%. After several tens of seconds, a transmission of 16% is achieved and the non-transparent switching film 5 is converted to a transparent light-yellow layer. The layer thus formed comprises semiconductive $GdH_x$ ($x>2$) having a bandgap of about 2.5 eV.

Subsequently, the pressure cell is evacuated to a pressure of $10^{-2}$ mbar (1 Pa). Within 1 s, the transmission decreases from 16% to approximately 5%, and after several tens of seconds, it decreases further to approximately 2%. Next, air is admitted up to a pressure of 5 bar. After several tens of seconds, the transmission has decreased further to 0.6%. Apparently, the presence of oxygen or moisture has a strong influence on the velocity of the dehydration process. In this state, the switching film comprises metallic $GdH_x$ (x<2).

The switching film 5 of $GdH_x$ (x<2) having a very low transmission is converted to a transparent switching film of $GdH_x$ (x>3) within 50 ms by renewed exposure to hydrogen. The conversion between both compositions is reversible; an optically switching film is obtained by the supply or discharge of hydrogen.

Figure 2:
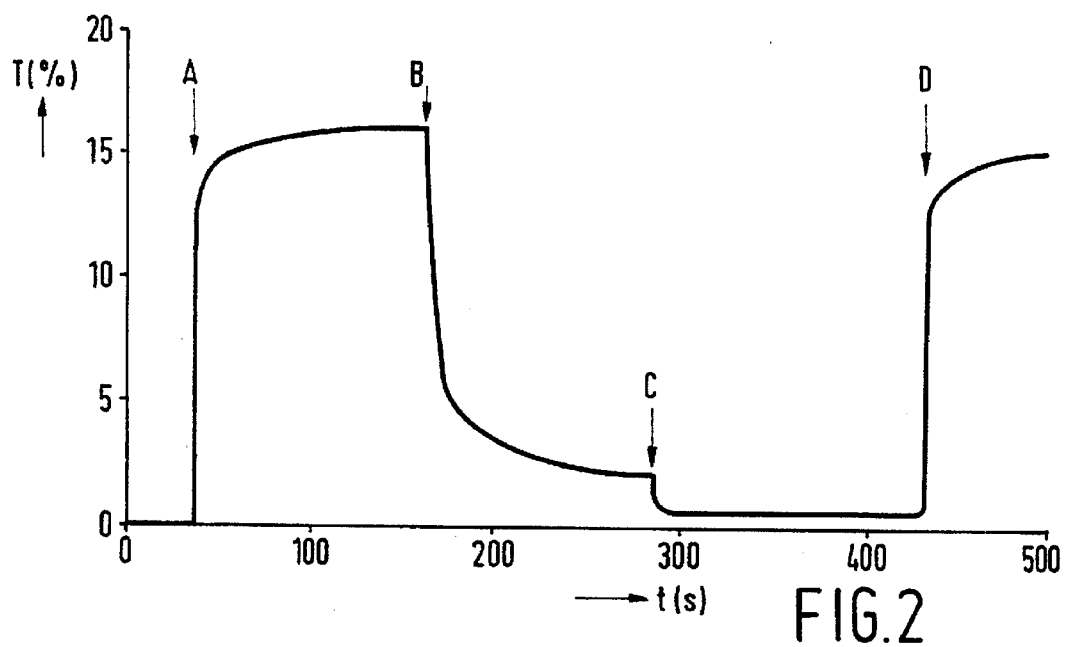
FIG. 2 shows the transmission T (in %) at a wavelength of 550 nm as a function of time t (in seconds) when the switching device in accordance with the invention is being exposed, or not being exposed, to hydrogen.

FIG. 2 shows the transmission T in % at wavelengths between 500 and 800 nm of the sample as a function of time t in seconds during the above-described experiment. At the point of time A, hydrogen is allowed to enter the pressure cell up to a pressure of 5 bar. At the point of time B, the pressure cell is evacuated to a pressure of $10^{-2}$ mbar. At the point of time C, air is admitted up to a pressure of 5 bar. At the point of time D, hydrogen is admitted again up to a pressure of 5 bar.

Exemplary Embodiment 2

Figure 3:
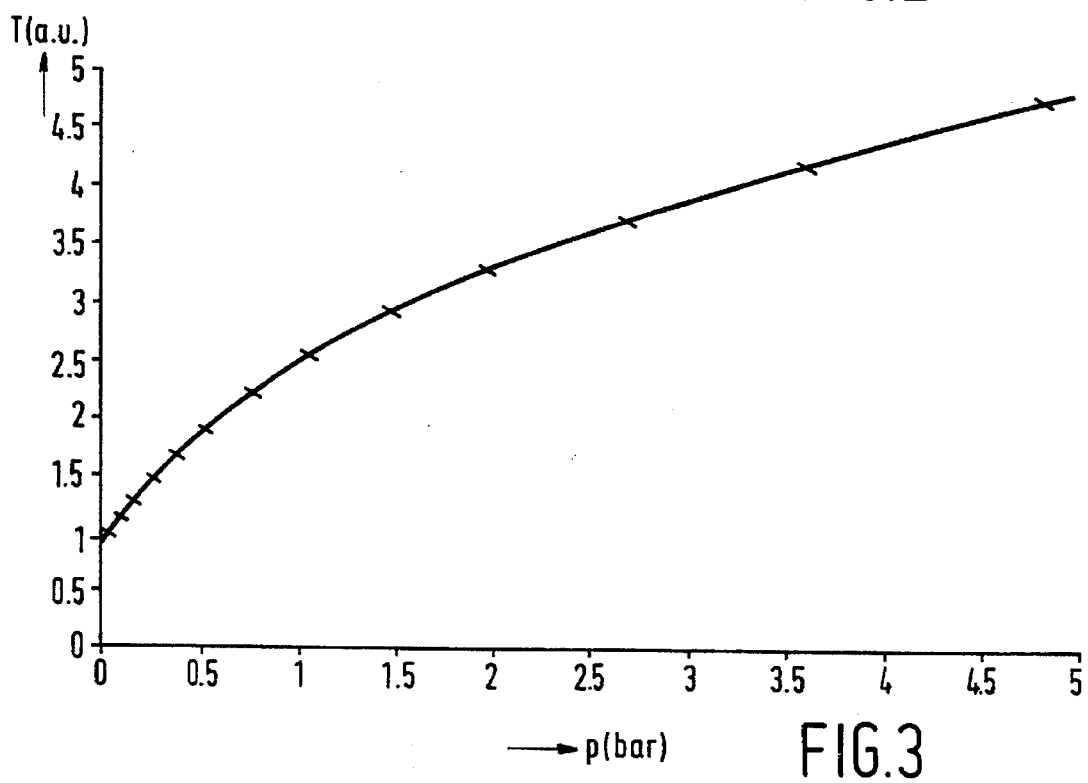
FIG. 3 shows the relationship between the transmission T (in arbitrary units a.u.) and the pressure p (in bar) of the switching device in accordance with the invention.

It has been found that there is a relation between the transmission of the sample and the hydrogen pressure in the range between $10^{-5}$ and 5 bar. FIG. 3 shows the relation between the transmission T (in arbitrary units a.u.) of a sample having an 1 µm thick gadolinium layer and a 10 nm thick palladium layer as a function of the hydrogen pressure p (in bar). In this manner, the switching device described herein can be used as a sensor for hydrogen pressure: the measured transmission can be translated directly into hydrogen pressure.

The switching device in accordance with the invention, which comprises a switching film of gadolinium, can be reversibly converted from a metallic, non-transparent state to a semiconductive, transparent state by an exchange of hydrogen. Said conversion takes place very rapidly at room temperature. Said switching device can be used, inter alia, as an optical switching element, as a sensor for hydrogen, and in display screens with variable transmission.

We claim:

1. A switching device comprising a substrate and a thin switching film containing a metal compound, characterized in that said metal compound contains a gadolinium hydride phase which can be reversibly switched from a low hydrogen content metallic to a supersaturated hydrogen-rich semiconductive composition by an exchange of hydrogen.

2. A switching device as claimed in claim 1, characterized in that the switching film is provided with a catalytically active layer for the dissociation of a hydrogen-containing compound.

3. A switching device as claimed in claim 2, characterized in that the catalytically active layer contains a metal selected from the group formed by palladium, platinum and nickel.

4. A switching device as claimed in claim 2, characterized in that the catalytically active layer has a thickness in the range from 2 to 25 nm.

5. A switching device as claimed in claim 1, characterized in that the switching film has a thickness in the range from 100 to 1,000 nm.

6. A switching device as claimed in claim 2, characterized in that the hydrogen-containing compound is $H_2$.

7. A switching device as claimed in claim 1, characterized in that the switching film can be reversibly switched from a non-transparent, metallic state to a transparent, semiconductive state.

* * * * *